US008672849B2

(12) United States Patent
Andreuccetti et al.

(10) Patent No.: US 8,672,849 B2
(45) Date of Patent: Mar. 18, 2014

(54) METHOD AND APPARATUS FOR ULTRASONIC DETECTION AND IMAGING OF HEMODYNAMIC INFORMATION, PARTICULARLY VENOUS BLOOD FLOW INFORMATION

(75) Inventors: Fabio Andreuccetti, Scandicci (IT); Piero Tortoli, Florence (IT)

(73) Assignee: Esaote S.p.A., Genoa (IT)

( * ) Notice: Subject to any disclaimer, the term of this patent is extended or adjusted under 35 U.S.C. 154(b) by 184 days.

(21) Appl. No.: 13/322,544

(22) PCT Filed: Aug. 27, 2010

(86) PCT No.: PCT/EP2010/062556
§ 371 (c)(1),
(2), (4) Date: Dec. 19, 2011

(87) PCT Pub. No.: WO2011/023797
PCT Pub. Date: Mar. 3, 2011

(65) Prior Publication Data
US 2012/0089027 A1   Apr. 12, 2012

(30) Foreign Application Priority Data
Aug. 31, 2009   (IT) .............................. GE2009A0070

(51) Int. Cl.
*A61B 8/08* (2006.01)
(52) U.S. Cl.
USPC .......................................... 600/443; 600/459

(58) Field of Classification Search
USPC .......................... 600/437, 440, 441, 453–459
See application file for complete search history.

(56) References Cited

U.S. PATENT DOCUMENTS

| 5,615,680 A | 4/1997 | Sano |
| 5,785,655 A | 7/1998 | Goodsell |
| 2009/0105594 A1 | 4/2009 | Reynolds |
| 2010/0022884 A1 | 1/2010 | Ustuner |

FOREIGN PATENT DOCUMENTS

| WO | 0068697 | 11/2000 |
| WO | 0171376 | 9/2001 |
| WO | 2009072092 | 6/2009 |

*Primary Examiner* — Parikha Mehta
(74) *Attorney, Agent, or Firm* — Themis Law

(57) ABSTRACT

A method for ultrasonic detection and imaging of hemodynamic information includes the steps of transmitting ultrasonic pulses into a body, which are generated by an array of electro-acoustic transducers arranged in a predetermined order and design; receiving reflected pulses with an array of receiving electro-acoustic transducers, which generate receive signals upon stimulation of the reflected pulses, the succession of pulses transmitted to or received from the body being focused along one or more scan lines; generating a Doppler frequency shift signal resulting from the reflection of pulses transmitted by a blood flow into a vessel intersected by the scan line, in a point and along the scan line, or along a direction of propagation of a pulse; determining the direction of blood flow velocity from the average frequency value of Doppler shift frequencies; and displaying the direction of blood flow velocity by graphical and/or chromatic representation differentiating opposite directions.

20 Claims, 4 Drawing Sheets

Velocity spectra from Doppler frequency signals

METHOD AND APPARATUS FOR ULTRASONIC DETECTION AND IMAGING OF HEMODYNAMIC INFORMATION, PARTICULARLY VENOUS BLOOD FLOW INFORMATION

FIELD OF THE INVENTION

The present invention relates to a method for ultrasonic detection and imaging of hemodynamic information, particularly venous blood flow information, which comprises the steps of acquiring and displaying Doppler data from a subject under study in an ultrasound system,

BACKGROUND OF THE INVENTION

The use of ultrasound beams for non invasively detecting velocity information of moving reflectors in a body under study is a well known technique. Several alternative ways are known and currently used for determining the velocity of a scatterer from the frequency or phase shift, which affects a back-scattered ultrasound beam according to the Doppler effect.

One of these methods is the so called Multigate Doppler processing method, which includes the steps of:
a) transmitting ultrasound waves into the subject under study;
b) generating back-scattered signals in response to the ultrasound waves back-scattered from the subject under study;
c) generating a plurality of Doppler signal samples representing a predetermined range of depth increments within said subject in response to said back-scattered signals;
d) generating a plurality of Doppler frequency signals representing said predetermined range of depth increments in response to said Doppler signal samples; and
e) displaying a first Doppler graph representing said Doppler frequency along a first axis and said range of depth increments along a second axis in response to said Doppler frequency signals.

In particular, Multigate Doppler processing is a PW Doppler technique, which allows dividing in a predefined range several smaller sample volumes corresponding to a certain number of successive depths increments along a transmitted beam emitted toward a bigger sample volume (gate) within a subject under study, in which Doppler frequency shift profile has to be determined. Doppler frequency profiles as a function of said depths increments means the velocity profiles of moving particles within said succession of smaller sample volumes. The processing of the Doppler signal samples, backscattered from the subject at each of said smaller samples volumes, i.e. the depths increments, is carried out essentially in parallel.

The above equivalence between sample volumes and depth increment along a transmitted beam is due to the fact that in order to acquire Doppler data with a PW technique, a pulsed ultrasound beam has to propagate along a direction, preferably at an angle related to the direction of motion of the reflectors.

A number of other different methods for ultrasonic detection of hemodynamic information are known and widely used in the art, and allow the determination of the average Doppler shift frequency and hence the average blood flow velocity in a predetermined point, or the spectral representation of Doppler shifts in a predetermined point, and show the distribution of the velocities of the blood particles of said flow in said point.

A method commonly known as CFM (Color Flow Mapping), which is used for determining the average Doppler shift frequency and hence the average velocity of a blood flow, consists in determining, for a predetermined point at one vessel, the mean of the spectral distribution of Doppler shift frequencies of ultrasonic pulses in said point. As an acquisition and processing method, CFM is known and widely used. See for instance U.S. Pat. No. 5,246,006. The ultrasonic signals are transmitted, received and processed to detect, for predetermined points along a predetermined scan line, the average spectrum frequency value in said point. Said average frequency is an estimate of the average displacement velocity of the reflector that moves through said point and hence of blood flowing through said point.

The visual result of the CFM method includes indication of the flow direction by one of two different colors, each being uniquely associated with one of the two directions, towards and away from the probe. Furthermore, the hue of said color indicates the intensity of the signal and hence the flow and/or the modulus of the average velocity.

As a rule, at the same time as Doppler processing of ultrasonic signals, a morphological (anatomic) image is also generated along a scan plane in the so-called B-Mode, particularly along a scan plane that contains the scan line/s used for CFM detection. The signals required for generation of the B-mode image are generally transmitted, received and processed alternating with transmission, reception and processing of Doppler signals.

Colors are added to the pixels of the B-mode image that coincide with the area or point at which the Doppler frequency shift has been detected.

Since a pulse of finite length is transmitted, the pulse will have a specific bandwidth and not only the fundamental frequency. Furthermore, within each sample volume (gate), several different kinds of moving reflectors can be provided so that the backscattered wave have a specific bandwidth and a specific spectral distribution of the frequencies within said bandwidth.

In addition to determining the average velocity value, i.e. the component of the mean frequency of the spectrum of Doppler frequency shifts, Doppler techniques are known, in which the entire spectrum of Doppler frequencies associated with a given sample point or volume is extracted. As already indicated above, these methods, known as Pulsed Wave (PW) methods, require more complex processing of ultrasonic signals, due to the much larger amount of information to be processed in comparison to CFM. An extension of the PW technology is the so-called Multigate which includes sequential Doppler spectrum detection through multiple sequential points (known as gates), arranged along a scan line, or a part of it, for reconstructing the velocity profile along said line.

The Multigate method is described in detail in the following documents:
P. Tortoli, G. Manes, C. Atzeni, Velocity profile reconstruction using ultrafast spectral analysis of Doppler ultrasound, IEEE Transactions on Sonics and Ultrasonics, Vol. SU-32, N. 4, pp. 555_561, July 1985;
P. Tortoli, F. Andreuccetti, G. Manes, C. Atzeni, Blood Flow Images by a SAW-Based Multigate Doppler system, IEEE Transactions on Ultrasonics, Ferroelectrics & Frequency Control, vol. 35, n. 5, pp. 545-551, September 1988;
P. Tortoli, F. Guidi, G. Guidi, C. Atzeni, Spectral velocity profiles for detailed ultrasound flow analysis, IEEE Trans.

on Ultrasonics, Ferroelectrics & Frequency Control, vol. 43, n. 4, pp. 654-659, July 1996;
An FFT-Based Flow Profiler for High-Resolution In Vivo Investigations, Piero Tortoli et al. Ultrasound in Med. & Biol. Vol. 23 No. 6 pp. 899-910, 1997;
U.S. Pat. No. 6,450,959.
Additional details of the CFM and PW methods may be found in the following documents:
U.S. Pat. No. 4,913,159, U.S. Pat. No. 4,817,618, U.S. Pat. No. 5,724,974 and WO 01/71376.

As shown by the above documents, the disclosures of which are incorporated herein by reference, the above techniques have been long known and widely used. The technology known as Multigate or Multigate Spectral Doppler allows for a quick real-time determination of the spectral profile of Doppler shifts according to the depth of penetration of ultrasonic pulses into the body under examination, with no excessive burden on processing units. The spectra of Doppler frequencies and/or the corresponding velocities are represented as frequencies or corresponding velocities along a first axis and as depths along a second axis of a Cartesian coordinate system.

As clearly shown by the description of the above techniques, all these techniques are based on the Doppler effect and do not allow assessment of the direction of a moving reflector and the direction of the blood flow when the axis of the beam of acoustic pulses, i.e. the direction of propagation thereof, are perpendicular to the displacement direction of the reflector. Indeed, the frequency shift according to the Doppler effect depends from the angle of propagation of a beam impinging against a moving reflector and the function in a cosine which gives a zero factor when the angle of incidence of the beam is 90°.

In PW Doppler in general, and particularly in Multigate technologies, the whole frequency content of the received echo signals corresponding to the back-scattered ultrasound beam by a certain sample volume is determined. When the direction of propagation of ultrasounds is perpendicular to the moving reflector and in a specific case of application of the present invention to blood flow direction, the spectral frequency distribution at the sample volume (gate or depth increment) is symmetric with respect to the line that corresponds to the zero Doppler frequency shift and hence to the zero velocity. On the other hand since in such kind of representation the brightness of the image corresponds to the intensity of the received signal and thus to the number of moving reflectors which are present in a certain sample volume, in the image displayed, in which the Doppler frequency signals of each sample volume are depicted one adjacent to the following sample volume according to the order of sequence of said sample volumes, using the entire frequency content of the Doppler frequency signals at each sample volume provides for a better determination of the sample volumes, in which the flow is considerable, and also the determination of the axis of propagation of the flow. On the other hand when the incidence angle of the beam relative to the flow direction is 90° or approximately 90°, it will not be possible to determine the direction of the flow since the Doppler frequency distribution within the spectrum of the Doppler frequency signal is symmetric being composed of specular positive and negative spectral components.

Multigate technology can be used for simultaneously highlighting and imaging multiple vessels at different penetration depths, i.e. at different distances from the origin of the ultrasonic pulses, within the overall range of penetration depth increments of the Multi-gate process.

In short, with prior art technologies, when the displacement direction of the reflector, and hence of a blood flow, is perpendicular to the direction of the axis of propagation of the incident beam of ultrasonic pulses, neither the CFM method, nor the PW, and particularly the Multi-gate method, allow an assessment of blood flow direction.

Contrary to what might appear, the above condition, in which the displacement direction of the reflector and hence of blood flow, is perpendicular to the direction of the axis of propagation of the incident beam of ultrasonic pulses, is not a rare condition in diagnostic imaging. For example, in hemodynamic imaging of cerebral vessels in the cranium, there are only a few windows through which the ultrasonic beam can be directed to said vessels. Unfortunately, the direction of the ultrasonic pulse beam is often oriented perpendicular to the flow in said vessels.

Furthermore, it is often needed or desired to simultaneously image the flow conditions in adjacent or parallel vessels at different penetration depths of the ultrasonic beam, whereby the direction of the beam axis or the direction of propagation of the acoustic front is fixed and determined by the requirement that all vessels to be imaged must be intersected thereby.

Further difficulties arise if Doppler imaging is used with venous blood flow. Here, vessels have a small size and the venous blood flow is relatively slow. Furthermore blood flux is not constant but varies according to heart cycle and to the inspiration expiration cycle, so that, for each sample volume, blood flow can vary its velocity from a maximum velocity to nearly zero or even to a negative velocity, i.e. to an opposite flow direction. This has the effect that the frequency signal will pass from a maximum value to a value which can be approximately zero or negative and the displayed signal will blink or even change color in the displayed Doppler graph. The variation of the status of appearance of the pixels in the image representing the value of the frequency signals will change from a certain color and brightness when a flux is detected, i.e. when there are moving blood particles to a quite black and/or very low brightness status of appearance when the flux is absent or very slow.

A particular application in which these conditions occur is simultaneous determination of blood flow characteristics in Galen's vein, middle internal cerebral vein and Rosenthal's vein. The determination of venous blood flow in these veins seems to have a considerable clinical and diagnostic relevance for early diagnosis of multiple sclerosis, as reported in Chronic Cerebrospinal Venous Insufficiency in Patients with Multiple Sclerosis, Paolo Zamboni et al., J. Neurol. Neurosurg. Psychiatry, 5 Dec. 2008. Now, in this case the cranial windows through which ultrasonic pulses are transmitted for acoustic treatment of the deep regions containing the veins, the blood flow of which has to be controlled for diagnostic purposes, are such that the above unfavorable condition occurs and the direction of blood flows is not currently detectable.

SUMMARY OF THE INVENTION

The invention addresses the problem of providing a method for detection and imaging of hemodynamic information, particularly venous blood flow information, which allows assessment of blood flow direction even in the most unfavorable conditions, especially in the condition in which the blood flow direction is perpendicular to the axis of the ultrasonic pulse beam transmitted into the body under examination.

A further object of the invention is to ensure the above result without requiring longer times for Doppler mode acquisition and processing of ultrasonic diagnostic images.

The present invention fulfills the above objects by providing a method for ultrasonic detection and imaging of hemodynamic information, particularly venous blood flow information, which is a method for acquiring and displaying Doppler data from a subject under study in an ultrasound system, said method comprising the following steps:

a) transmitting ultrasound waves into the subject under study;

b) generating back-scattered signals in response to the ultrasound waves back-scattered from the subject under study;

c) generating a plurality of Doppler signal samples representing a predetermined range of depth increments within said subject in response to said back-scattered signals;

d) generating a plurality of Doppler frequency signals representing said predetermined range of depth increments in response to said Doppler signal samples;

e) displaying a first Doppler graph representing said Doppler frequency along a first axis and said range of depth increments along a second axis in response to said Doppler frequency signals;

f) generating Doppler mean frequency signals at each of said range depth increments from said Doppler frequency signals;

g) displaying a second Doppler graph representing said Doppler mean frequency along said first axis and said range depth increments along said second axis by setting the parameters defining a status of appearance of the pixels forming the displayed image of said second Doppler graph in such a way as to visually differentiate said pixels from the pixels of the image of said first Doppler graph;

h) repeating the above sequence of steps with a specific repetition frequency;

i) setting the persistence of the status of appearance of the pixels forming the image of said second Doppler graph in such a way that said pixels retain their status of appearance regardless of any attenuation or termination of said Doppler frequency signals for a predetermined period of time and/or until new Doppler signals with greater absolute mean frequency values are generated from Doppler signal samples acquired during at least one of repeating steps h);

j) said new values of said Doppler mean frequency signals being used to upgrade the displayed image of said second Doppler graph by setting the status of the appearance of the pixels forming said image.

According to a first improvement of the above method, an additional step is provided of filtering out the low frequency component of the Doppler frequency signals before generating the Doppler mean frequency signals.

This provides an enhancement of the polarization effect of the mean Doppler frequency values relatively to the direction of flow.

According to one embodiment, the above mentioned step g) consists in enhancing the brightness of the pixels forming the image of said second Doppler graph.

This step can be provided either alone or in combination with a further step consisting in reducing the brightness of the pixels forming the image of the first Doppler graph.

In order to further enhance the indication of direction, by which a trace of brightness enhanced pixels is either on the left or on the right side of the zero value for the Doppler frequency or velocity in a graphic representation in a Cartesian system, with one axis representing Doppler frequencies or velocities and the other axis the depth increments or sample volumes, a step is performed of changing frequency scale along the corresponding axis representing the values of the Doppler frequency.

The different scale can be chosen in such a way that it enlarges the dimensions of the image of said second graph in relation to the dimensions of said first graph along said first axis.

The same effect could be obtained by providing an enhancing parameter, which is multiplied to achieve the determined values of the mean Doppler frequencies.

As mentioned above, the method is suitable for a subject under study comprising at least a blood vessel and blood flux in said vessel, having a flux velocity varying in time between a maximum velocity and a velocity which is approximately zero or in the opposing direction. In this case the predetermined range of depth increments is set to cover the entire cross section of said at least one vessel, the Doppler frequency signals and the Doppler mean frequency signals being representative of the velocity of the blood flux in the vessel at said depth increments. Furthermore, the method is applied in a manner that the persistence of the status of appearance of the pixels forming the image of said second Doppler graph is maintained until new Doppler signals with greater absolute mean frequency values are generated from Doppler signal samples acquired during at least one of repeating steps h) coinciding with a greater, in absolute value, blood flux velocity.

Furthermore, a method according to the invention can be applied to back-scattered signals which are received from a first region of interest within said subject resulting in said Doppler signal samples, and from at least second or more regions of interest within said subject.

If possible in the above case, the transmitted ultrasound waves comprises an ultrasound beam optimized for Doppler data acquisition, which is directed along a direction crossing at least two or more of said region of interests.

Also in this embodiment, said regions of interests are different blood vessels and a plurality of Doppler signal samples are generated in response to said back-scattered signals representing a predetermined ranges of depth increments, each of which crosses at least partially one of said vessels.

As usual in methods of displaying echographic Doppler data, the present method comprises additional steps consisting in acquiring and displaying B-mode data from the subject under study in an ultrasound system.

Said steps consist in generating B-mode data for a region of interest containing the subject under study, in displaying the B-mode image, and in displaying in a superimposed way on said B-mode image, with the scan line along which the Doppler beam focused and with the range of depth increments on the corresponding region of interests.

The method according to the above invention allows extracting direction information of blood flows based on the fact that, in practical cases, it will be very improbable that the transmitted beams will have an angle of incidence relative to the flux direction which is perfectly 90°, which is the condition in which no frequency shift will be generated. Under normal practical conditions it is more probable that the angle of incidence will be very near to 90° but not quite 90°, and will vary also within a tolerance in time due, for example, to the motion of the body under study or the motion of the person holding and orienting the ultrasound probe. In this condition, there will be a very low Doppler frequency shift of the back-scattered waves relative to the frequency of the transmitted waves. So the Doppler frequency shift spectrum for a sample will contain direction information due to very small frequency shifts either positive or negative, and the processing and displaying steps of the Doppler frequency signals according to the present invention help in enhancing and displaying such frequency shifts, in order to extract and indicate also the direction of the moving scatterer, i.e. the blood flux in a vessel.

According to a further improvement of the invention, the above method steps can be provided in combination with additional steps allowing a further differentiation of the angle of incidence of the transmitted ultrasound waves relative to the direction of motion of a moving scatterer, such as the direction of flow of a bloodflow.

According to these further steps, a transmit and a receive array of ultrasound transducers is provided, respectively for emitting ultrasound waves upon excitation by means of excitation signals, said emitted waves being transmitted to the subject under study, and for detecting the ultrasound waves backscattered from the subject under study and generating corresponding receive signals, said arrays of transducers having a certain aperture. The method according to the invention provides that the ultrasound waves are transmitted using a first sub-array of the transmit array of transducers, said sub-array being formed by only a part of the ultrasound transducers of the transmit array, having a first aperture different from the aperture of said transmit array, and generating an ultrasound beam having a direction of propagation. That direction of propagation is different from the direction of propagation of an ultrasound beam generated by the complete transmit array of transducers, said direction of propagation of the ultrasound beam emitted by said sub-array defined to at least partially cross one or more region of interests within the subject under study.

In that situation, the back-scattered ultrasound beams are received by a second sub-array of the receive array of transducers or by the complete array of transducers.

The second sub-array of receive transducers may be different from the first sub-array of receive transducers.

According to a further improvement, the transmit and receive array of transducers consist of the same array of transducers in combination with a switch connecting alternatively the transducers of the array to a generator of excitation signals of the transducers and to a processing device of the receipt signals generated by the backscattered ultrasound waves impinging on said transducers.

Due to the above method steps, during transmission only some of the transmitting electro-acoustic transducer elements are used, which form a sub-array of transducers that is eccentric relative to the central axis perpendicular to the complete array of transducers. The central axis of said sub-array of transducers is thus laterally off-set relative to the central axis of the complete array. When transmitting, electro-acoustic elements of the sub-array are excited in such a manner that the transmit pulse beam is focused against a subject. The above introduced eccentricity of the sub-array of transducers relative to the central axis of the entire array of a probe determines a slight steering of the beam generated by the subarray in the direction towards the center axis of the entire array.

Considering the situation, in which the entire array is excited to generate a transmit beam focused on a volume sample, it appears clearly that the beam generated by the eccentric sub-array and focused on the same volume sample has a different angle of incidence than the beam generated by the entire array, and if the angle of incidence of the beam generated by the entire array is 90°, than the angle of incidence of the beam generated by the sub-array is different from 90° so that Doppler frequency signals are enhanced.

The backscattered ultrasound waves can be received by means of a sub-array, which can be a different sub-array from the one transmitting the ultrasound beam or the entire array, such to have as much signal intensity as possible for the received signals.

In alternative to the above, eccentricity may be specularly obtained by operating on the receiving elements instead of the transmitting elements. Nevertheless, this will require the use of a smaller number of receiving elements, and hence cause a reduction of sensitivity that cannot be easily compensated for. Conversely, any reduction in the number of transmitting elements may be compensated for by pulsing a higher voltage.

Double eccentricity may be also provided, in relation to the center line, by using a first sub-array of transducers determining a first aperture, which are on one side of the center of the entire array at least along one dimension of the array for generating the ultrasound transmit beam, and a second sub-array of transducers determining a second aperture, which are on the other side of the center of the entire array at least along one dimension of the array for receiving the backscattered ultrasound beams.

The first and second sub-array and the corresponding first and second apertures can be symmetric relative to the center of the entire array of transducers at least relative to one of its dimensions.

Indeed, transducers can be linear transducers or two dimensional transducers. In one case the center of the transducer and the symmetry relative to it is clearly defined. In the case of a two dimensional array, different alternatives can be chosen, since the center of the transducer is the point which is at the center of the two directions along which the transducers are aligned, and the definition of the position of the sub-array relative to the center depends on the position along each one of said two directions.

Nevertheless, the above alternative embodiment, in addition to reduced sensitivity, as mentioned above, has an excessive displacement of the window of view from the orthogonal position, which would prevent simultaneous imaging of vessels disposed substantially parallel to the probe, like in the case of the above mentioned cerebral vessels. However, in other cases this receiving mode might be used.

In a variant embodiment of the invention, the first and second sub-array and the corresponding first and second apertures can be asymmetric relative to the center of the entire array of transducers at least relatively to one of its dimensions.

Considering a one dimensional array of transducers among the transducers, those that are used for beam generation are eccentric in relation to the direction of propagation of the ultrasonic pulse beam, which corresponds to that which would have had an ultrasonic beam generated by all the elements of the array of electroacoustic transducers. By providing the focusing point/s on said direction of propagation, to focus an ultrasonic beam generated only by part of the transducers of the array positioned in an area of the array, which is eccentric relative to the direction of propagation, the direction of propagation of the beam shall necessarily be laterally off-set, thereby introducing the above mentioned slight steering. The above arrangement provides for angles of incidence of the transmit pulse beam relative to blood flow direction of about 87° to 85° when the angle of incidence of the beam generated by the entire probe would have been 90°.

In practice, considering a phased array probe, which comprises a linear array of 128 elements, the direction of propagation of the beam is the center axis, which separates the array of adjacent electro-acoustic elements into two halves, each comprising 64 elements. The center axis of the sub-array consisting in one of the two halves of the linear array of electro-acoustic elements is provided at the 32nd or 96th element, whereby if the ultrasonic transmit pulse beam is focused toward one or more points along said central axis of the entire array, the direction of propagation of the beam generated by the sub-array will be inclined relatively to said central axis and intersect it at the focusing points.

Thus, the above described improvement of the present invention combines the method steps of: improving the multigate processing of PW Doppler data acquisition and display, in which a plurality of points or sample volumes are defined along at least one scan line, wherein the points or sample volumes represent a range of increments of the penetration depth of ultrasonic pulses into the body under examination along said at least one scan line;

the backscattered ultrasound beams being processed in order to generate Doppler frequency signals for each of said points or sample volumes and said Doppler frequency signals are displayed in a graph as a function of penetration depth in that graph;

said increments of penetration depth being represented along one axis and the Doppler frequencies being represented along a second axis perpendicular to the former;

generating Doppler mean frequency signals, which are also displayed in a superimposed way on the graph by enhancing the appearance of the pixels representing the mean frequency values relative to the pixels representing the Doppler frequency signals as a function of depths increments; and providing at least for the generation of the transmit beam a different aperture of the array, such that the direction of propagation of the ultrasound beam is stirred relatively to the one which would be obtained under traditional ways of driving the array.

These features, in combination with the other above discussed features, further enhance the detection of the direction of the moving scatterers, such as blood flux, also when the angle of incidence of the transmit ultrasound waves is perpendicular to the direction of movement of the scatterers.

In a particular application, designed for Doppler imaging of internal cerebral veins, particularly for simultaneous Doppler imaging according to the method according to the present invention, eight equally spaced foci are provided on the first axis of the ultrasonic pulse beam, which correspond to a limitation of successive penetration depth increments, located at the following penetration depths: 25, 40, 55, 70, 85, 100, 115, 130 mm.

Advantageously, a phased array probe is used in the method of the present invention.

According to a variant embodiment, the method of the present invention may include parallel acquisition and overlapped or side-by-side display of the B-mode gray-scale image of the area that contains the vessels, whose blood flow has been detected.

As it appears from the previous disclosure, the Multigate-based method of the present invention, when compared with the traditional CFM method, allows for simultaneous CFM imaging with both low PRF (involving high sensitivity but excessive aliasing, i.e. identification of vessels, but not their direction) and high PRF (involving low sensitivity, but identification of flow direction), which would not be feasible with the use of the CFM method only. This will simultaneously afford the same sensitivity as the one provided by the CFM method with low PRF and the same flow direction identification ability as that provided by the CFM method with high PRF.

The invention also relates to an ultrasound imaging system for implementing the method for ultrasonic detection and imaging of hemodynamic information, particularly venous blood flow information, which system comprises:

an ultrasonic probe comprising an array of transmitting and receiving electro-acoustic transducers, arranged according to a predetermined order and design;

each transmitting electro-acoustic transducer element having its own independent line for connection to a unit for generating and transmitting electric excitation signals for the corresponding electro-acoustic transducer element;

each receiving electro-acoustic transducer having its own independent line for connection to at least one processing unit;

at least one unit for multigate processing of image data, for generating Doppler frequency signals from the Doppler signal sample received from the sample volumes at different depths increments;

at least one processing unit for calculating the average frequency of signals of the Doppler frequency signals related to at least some of the sample volumes; and means for displaying a first Doppler graph representing said Doppler frequency along a first axis and said range of depth increments along a second axis in response to said Doppler frequency signals, and for displaying a second Doppler graph representing said Doppler mean frequency along said first axis and said range depth increments along said second axis. This is achieved by setting the parameters defining a status of appearance of the pixels forming the displayed image of said second Doppler graph to visually differentiate said pixels from the pixels of the image of said first Doppler graph.

In one embodiment, the apparatus may further comprise:
means for transmission and reception of electro-acoustic pulse beams for anatomic B-mode imaging;

and a receive signal processing unit for generating B-mode image data and means for displaying the B-mode image in side-by-side relation with the image that displays the average frequencies of the spectral profiles of Doppler shift frequencies and the spectral profiles of Doppler shift frequencies as a function of the penetration depth of the transmit ultrasonic pulse beam.

In this case, the system may further comprise means for graphically drawing a line on the B-mode image and for selecting said line as the line along which a beam for Doppler data acquisition has to be focused. This embodiment may further include:

means for selecting a predetermined range of depths increments along said line at one or more regions of said line;

means for calculating the beam focusing parameters for driving the transducers of the array of the probe to focus the beam at said line and for setting a receive signal processing unit of an ultrasound apparatus to extract and process the receipt signal contribution related to the ultrasound beams backscattered from each of the sample volumes corresponding to said depth increments;

means for tracking the position and orientation of the probe and determining the orientation of the line along which the ultrasound transmit beam will be focused and for displaying said line on the be mode image; and means for triggering the transmission of the ultrasound beam when the line, on which the beam is focused, coincides with the line drawn on the B-mode image.

In an additional improvement, the system is provided with switching means for connecting to the unit for generating and transmitting electric excitation signals, a number of selected transducers less than the total numbers of transducers of the array, said number of transducers being selected to form a sub-array of transducers having a aperture, which is different from the aperture of the complete array of transducers and eccentric relative to the center of said array of transducers;

and with switching means for connecting to the unit for processing receipt signals, a number of selected transducers of the array of receipt transducers, said number of transducers being selected to vary said number of transducers from the total number of transducers to a number less than the total number of the transducers, in order to form a sub-array of transducers having an aperture, which is different from the aperture of the complete array of transducers and eccentric relative to the center of said array of transducers.

In an additional improvement, said switching means are automatically driven by control means, which vary the number of selected transducers of the array of transmit transducers and/or of the array of receipt transducers by computing the corresponding aperture from the data determined by the physical law of propagation of acoustic waves and the orientation of the line drawn on the B-mode image, along which the transmit beam must be focused, and the position on that line of the sample volumes defined by said range of depth increments.

In another improvement, additional means can be provided, which vary the number and the position on the array of said transmit and or receipt transducers to be selected for maximizing the value of the maximum mean Doppler frequency detected.

Additional improvements of the invention will also be described in detail hereinafter.

BRIEF DESCRIPTION OF THE DRAWINGS

These and other features and advantages of the present invention will appear more clearly from the following description of a few embodiments, illustrated in the enclosed drawings, in which.

DETAILED DESCRIPTION OF EMBODIMENTS OF THE INVENTION

According to the present invention, Doppler signals are processed using a multigate spectral Doppler technique, which provides spectral profile information as a function of a depth of penetration. This is achieved by defining a plurality of focusing points along a line of view at different penetration depth increments of the ultrasonic pulse beam in a subject under study. Said focusing points are defined as volume samples, which correspond to the depth increments, and this definition is coherent since each ultrasonic beam has a transverse pattern and also an axial pattern which have finite dimensions.

Figure 1:
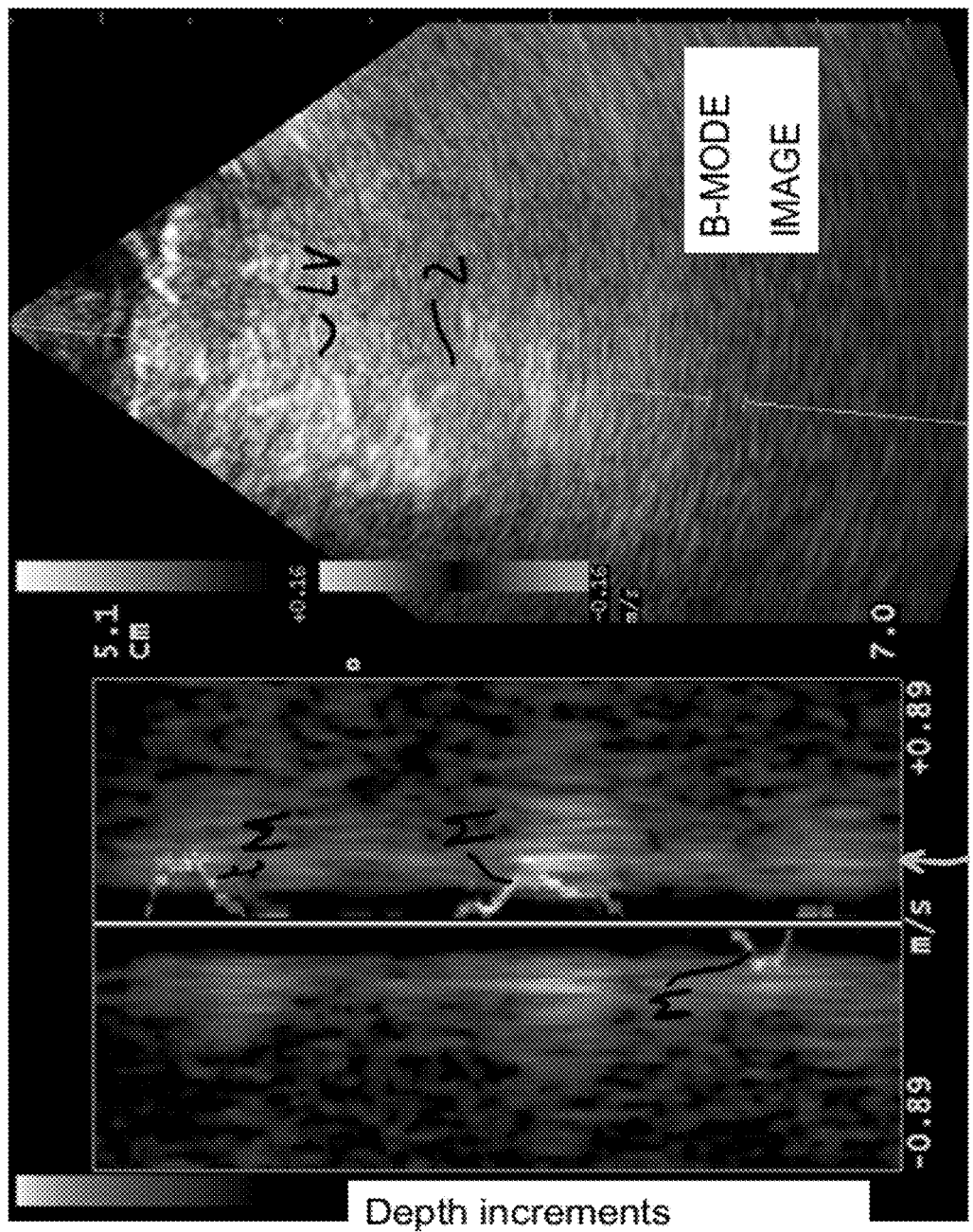
FIG. 1 shows an example of a screenshot showing hemodynamic information concerning deep cerebral veins, and particularly Galen's vein, the middle internal cerebral vein and Rosenthal's vein, as simultaneously detected by a method and apparatus according to the present invention, reproducing the velocities of the flows as derived from the spectral profiles of Doppler frequency shift and the average frequency of said spectral profiles in penetration depth ranges corresponding to the above veins.

Here, the Doppler frequency signals generated by the multigate processing have a spectral frequency distribution within a certain bandwidth, and the frequencies which are present in the spectrum of each Doppler frequency signal relative to each sample volume or depth increment are displayed as a function of said penetration depth increments of the beam, which is represented by the Y-axis of a Cartesian coordinate system, whereas the X-axis represents the Doppler shift frequencies, i.e. flow velocities (see the image on the left of FIG. 1).

Figure 4:
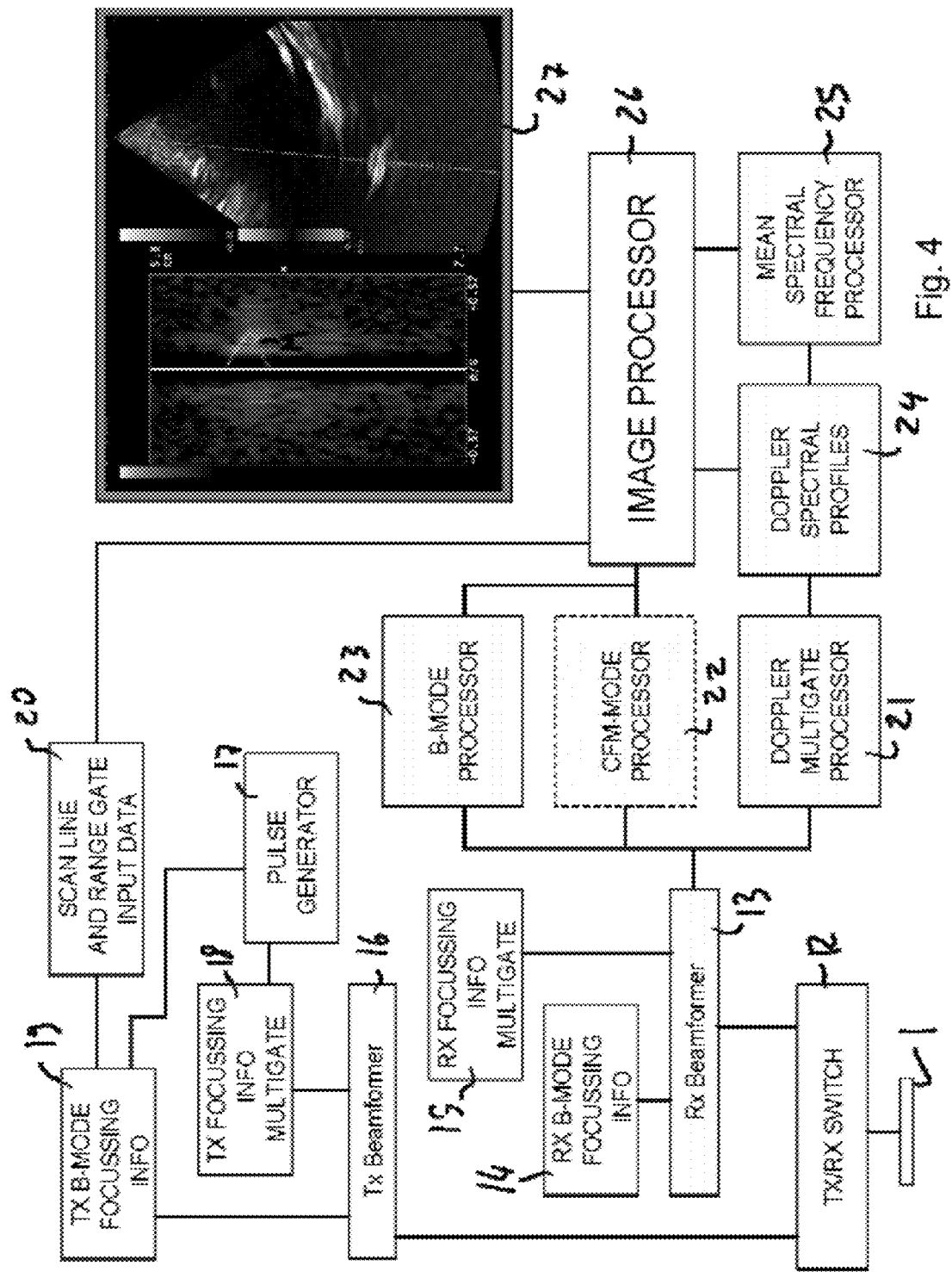
FIG. 4 is a block diagram of an apparatus for implementing a method according to the present invention.

As it appears from FIG. 1, the first graph, this means, the Doppler frequencies at the sample volumes, are represented by the two vertical grey stripes divided by a black area centered on the Y-axis at the zero velocity. Since the angle of incidence of the ultrasound beam indicated by LV in the B-mode image on the right-hand side of the image of FIG. 4 is about 90° in relation to the direction of flow in the vessels, the multigate processed image data is symmetric relative to the Y-axis crossing the X-axis at zero velocity value. The only information which can be obtained is the information relative to the depth increments or sample volumes, which coincide with the different vessels. This is shown by the higher brightness of the pixels at the level of specific depth increments. So, in the special condition of a beam which has an angle of incidence of 90° or about 90° relative to the flow direction, the traditional multigate Doppler processing and display can only give information on the position along the direction of propagation of the ultrasound transmit beam of a blood flow.

According to a method of the present invention, in order to extract also information about the direction of blood flow, the Doppler frequency signals are processed for determination of average frequency values at least for the sample volumes at specific penetration depth of the ultrasonic pulse beam. In particular, the penetration depths are the ones at which the brightness of the pixels in the Doppler graph reveals the presence of a flow.

Since it is highly improbable that the angle of incidence of the ultrasound beam relative to the direction of blood flow is precisely 90°, the Doppler frequency signals must contain a signal contribution, which relates to the direction of said flux but which are very small and cannot be revealed with a traditional way of processing and displaying said signals. The present method has shown that the mean Doppler frequency signals enhance the indication of the direction of the flow, since the spectral components of the Doppler frequency signals which are symmetric about the zero Doppler frequency will reciprocally cancel. Here it is clear that the term Doppler frequency in the present description and in the claims means Doppler frequency shift, which is equivalent with Doppler phase shift or velocity. Indeed, by determining the mean Doppler frequency for the Doppler frequency signals related to the sample volumes or depth increments coinciding with the position of the blood flows in the right hand part of FIG. 1, and displaying said values as a pixel trace in a superimposed way on the Doppler frequency graph representing the spectral components of each Doppler frequency signal, by using the same coordinate system the Doppler frequency profiles, i.e. the blood flow velocity profiles within each vessel appear as a pixel trace only on one side of the line passing through the zero frequency or velocity value, thus indicating the direction of the flow and also the velocity distribution of the flow within the lumen of the vessel. These images are represented by the arched lines indicated by M.

As shown, the combination of multigate techniques and the calculation of the average frequency of Doppler shift spectral profiles caused by the blood flows under examination can overcome the limitations of prior art technologies as briefly described above, namely the limitations of the Doppler imaging technique known as Color Flow Mapping, which are caused by the contrasting requirements of achieving sufficient signal sensitivity and detecting flow direction in setting pulse repetition frequency (PRF).

FIG. 1 relates to Doppler imaging of deep cerebral veins, particularly Galen's vein, the middle internal cerebral vein and Rosenthal's vein.

Ultrasound Doppler imaging of these veins is particularly indicative of the problems that this invention is designed to solve, because intracranial ultrasound imaging is limited by the presence of very few ultrasonic beam penetration windows in the cranium. Using these windows, the above mentioned vessels are located in a position, relative to the lines of view, in which the flow is actually perpendicular to the direction of penetration of the acoustic front and hence of the axis of ultrasonic pulse beams, if traditional techniques are used.

On the left side of FIG. 1, a diagram in which the Y-axis represents penetration depths and the X-axis represents Doppler shift frequencies, i.e. blood flow velocities, shows the spectral profiles as determined at different penetration depth increments along the line of view LV, on which the foci 2 of ultrasonic pulse beams are located. The spectral profiles are given by the areas of varying brightness. It may be observed that the spectral profiles clearly highlight denser and brighter zones that correspond to three vessels, i.e. Galen's vein, the middle internal cerebral vein and Rosenthal's vein, which are substantially parallel to each other and perpendicular to the possible line of view, considering the small size of the windows designed for the passage of ultrasonic pulses that are available in the cranium.

The graphs M of the mean Doppler velocity or frequency as a function of the depth increments show that the flows of the two vessels at lower depths are oriented in the same direction, whereas the flow of the third vessel, the one at higher depths, is directed opposite to those of the other two vessels.

According to an improvement that is shown in FIG. 1, parallel to Doppler imaging, anatomic B-mode imaging is performed, and the B-mode image is displayed adjacent to the one of spectral profiles and Doppler shift averages. This is shown on the right side of the image of FIG. 1. The B-mode image is typically a gray-scale image. Furthermore, a Color Flow Mapping Doppler image, also obtained parallel to the others, may possibly be displayed thereon.

The B-mode image shows the vessels, with the line of view LV and the focusing ranges 2 possibly set thereon.

For minimized processing burden and real-time imaging, a limited number of foci may be reset along the line of view, to define a predetermined number of range gates within a penetration depth increment or sample volume, in which the maximum and minimum end values can be also set. The number of foci along the line of view and the penetration depth range, i.e. the minimum and maximum end values of said range, may be set according to anatomic conditions and relevant requirements.

As a rule and particularly for intracranial Doppler imaging of deep cerebral veins, a number of eight foci has been selected to define a penetration depth range from 25 to 130 mm, said foci being located at depths of 25, 40, 55, 70, 85, 100, 115 and 130 mm.

During reception, the number of foci is the traditional number of 32 foci, which are dynamically focused.

A method according the present invention includes additional improvement steps, which assist enhancement obtained by the generation and display of the mean frequency signals, i.e. the direction of blood flow in the corresponding vessel in the image of FIG. 1.

Concerning the image, according to a first improvement of the invention, the brightness of the image of the first graph related to the display of the frequency components of the spectrum of each Doppler frequency signal at different depth increments is attenuated with respect to commonly used values. Such attenuation may be selected by users in a customized manner and/or according to predetermined fixed levels.

Another feature consists in having the low frequency components of the spectrum of each Doppler frequency signal massively filtered out, whereby the average obtained therefrom is more significant in terms of flow direction information.

According to still another improvement, the brightness and/or color of the image (pixel trace M) related to the graph representing the mean Doppler frequency as a function of depth increments can be incremented in order to be highlighted relative to the image on which it has been superimposed.

This enhancement can be carried out in an automatic way by determining the brightness of the pixels in the neighborhood of the pixel representing the values of the mean frequency.

Furthermore, in order to have a clearer indication of the direction of flow, the values of the mean frequency can be rescaled. A new scale can be defined for the X axis, which allows a zooming of the trace of pixels so that it ranges wider in the X direction. Alternatively or in combination, the scale can be maintained the same and the values of the mean frequency can be multiplied by an enhancing factor.

A further arrangement concerning the displayed image consists in providing an asymmetric persistence of the spectral average image. This is relevant for blood flows and particularly for venous flows which occurs during inspiration. Upon inspiration, the Doppler frequency signals and hence their representation is at a maximum, whereas intensity decreases with time, substantially disappears during expiration and reaches the maximum value again during the next inspiration step. This physiological condition would involve a progressive reduction of the spectral average plot in the displayed image. In order to prevent such fluctuation, at least the mean frequency signals but also the Doppler frequency signals are displayed and maintained at the maximum level throughout each entire inspiration and expiration cycle and are replaced by the display of new Doppler frequency signals and the corresponding mean frequency signals relative to the backscattered beams received during the new subsequent inspiration. Thus, signal persistence is asymmetric with reference to the inspiration and expiration cycle.

Said feature can be applied for every kind of moving scatterer, where velocity varies cyclically upon time between a maximum and a minimum value. In this case the displayed signals are relative to the ones determined during the phase in which the velocity is a maximum, and said image is maintained throughout the following phases of the cycle till the next phase when the velocity of the caterer is again at its maximum value. The new signals are then generated and displayed in substitution to the previous ones.

Throughout the present disclosure, ultrasound imaging is deemed to be part of the base knowledge of the skilled person, both in terms of anatomic ultrasound imaging, particularly using B-mode, and in terms of Doppler and color Doppler ultrasound imaging, i.e. spectral Doppler imaging and Doppler color flow imaging, such as the Color Flow Map or the like.

Besides the above mentioned documents, B-mode and Doppler ultrasound imaging has been long known in a number of different variants. A summary of Doppler imaging techniques has been published and is available for download from http://echoincontext.mc.duke.edu/doppler04.pdf that is part of an educational web site of Duke University. The authors of this summary are also the authors of the book "Doppler color flow imaging" by J A Kisslo, D B Adams, R N Belkin (1988), Churchill Livingstone.

Special reference will be made herein for simplicity, clarity and brevity purposes to the inventive method arrangements, which surpass the technical basics of common prior art methods and apparatus.

Concerning blood flow detection technologies, as anticipated above, a technology known as multigate has been known for about ten years. The theoretical bases of this technology are described in the following documents:

P. Tortoli, F. Guidi, G. Guidi, C. Atzeni, Spectral velocity profiles for detailed ultrasound flow analysis, IEEE Trans. on Ultrasonics, Ferroelectrics & Frequency Control, vol. 43, n. 4, pp. 654-659, July 1996;

Piero Tortoli et al., An FFT-Based Flow Profiler for High-Resolution In Vivo Investigations, Ultrasound in Med. & Biol., Vol. 23, No. 6, pp. 899-910, 1997;

Piero Tortoli et. Al., Detection of vascular hemodynamics through a high-speed velocity profiler, European Journal of Ultrasound, 9 (1999), 231-244;

and WO01/71376, which addresses a particular method of displaying flow velocity information.

Figure 2:
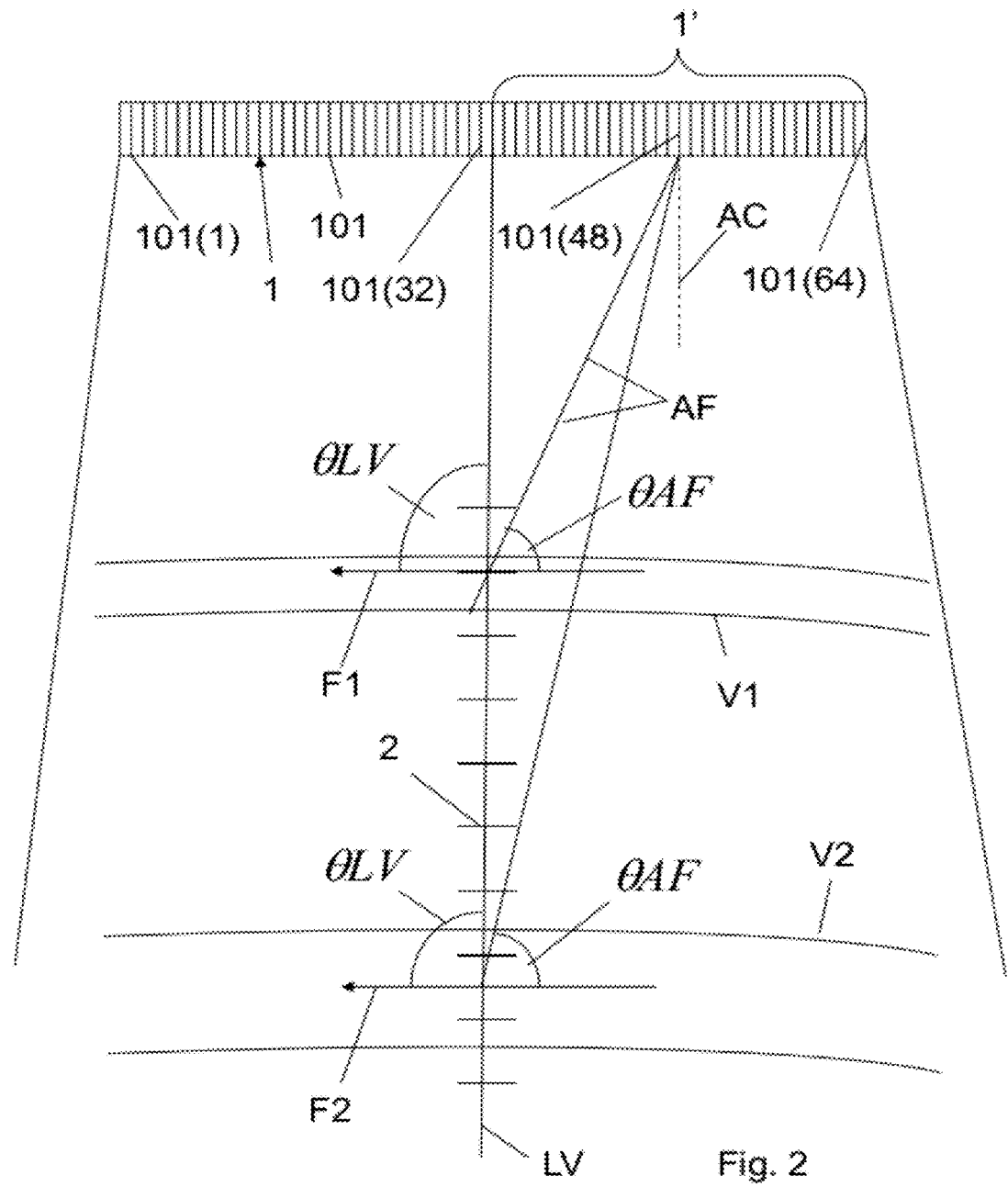
FIG. 2 schematically shows a phased array ultrasonic probe having 64 elements, and the transmission of an ultrasonic pulse beam according to a method of the present invention.
Figure 3:
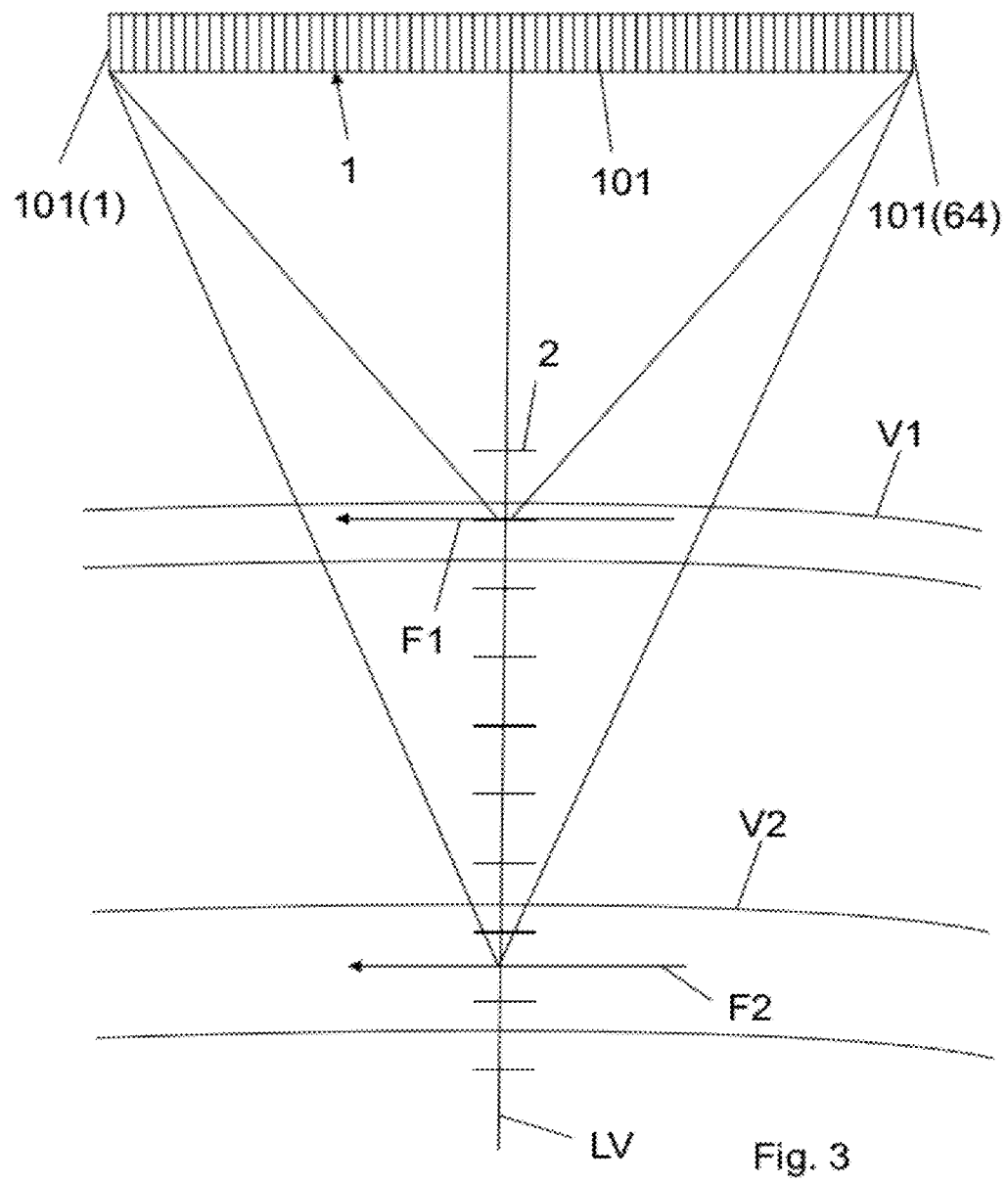
FIG. 3 is a view similar to FIG. 1 that shows how the received ultrasonic pulse beam is focused.

As it will appear more clearly from the following description of FIGS. 2 and 3, the effect obtained by means of the above disclosed method can be enhanced by applying improvements at the stage of transmission and/or receipt of the ultrasound signals.

According to these improvement, additional steps are provided, according to which a transmit and a receive array of ultrasound transducers is provided, respectively for emitting ultrasound waves upon excitation by means of excitation signals, said emitted waves being transmitted to the subject under study, and for detecting the ultrasound waves backscattered from the subject under study and generating corresponding receive signals, said arrays of transducers having a specific aperture. A method according to the invention provides that the ultrasound waves are transmitted using a first sub-array of the transmit array of transducers, said sub-array being formed by only a part of the ultrasound transducers of the transmit array and having a first aperture different from the aperture of said transmit array, and generating an ultrasound beam having a direction of propagation which is different from the direction of propagation, which would have been of an ultrasound beam generated by the complete transmit array of transducers. The direction of propagation of the ultrasound beam emitted by said sub-array is defined to at least partially cross one or more region of interests within the subject under study, while the back-scattered ultrasound beams are received by a second sub-array of the receive array of transducers or by the complete array of transducers.

The second sub-array of receive transducers may be different from the first sub-array of receive transducers. The transmit and receive array of transducers may consist of the same array of transducers in combination with a switch connecting alternatively the transducers of the array to a generator of excitation signals of the transducers and to a processing device of the receipt signals generated by the backscattered ultrasound waves impinging on said transducers.

Thanks to the above method steps, during transmission only some of the transmitting electro-acoustic transducer elements are used, which form a sub-array of transducers that is eccentric in relation to to the central axis perpendicular to the complete array of transducers. The central axis of said sub-array of transducers is thus laterally off-set relative to the central axis of the complete array when transmitting electro acoustic elements of the sub-array are excited in such a manner that the transmit pulse beam is focused against said subject. The above introduced eccentricity of the sub-array of transducers relative to the central axis of the entire array of a probe determines a slight steering of the beam generated by the sub-array in the direction towards the center axis of the entire array.

Considering the situation in which the entire array is excited in order to generate a transmit beam focused on a volume sample, it appears clearly that the beam generated by the eccentric sub-array and focused on the same volume sample would have a different angle of incidence than the beam generated by the entire array. If the angle of incidence of the beam generated by the entire array is 90°, than the angle of incidence of the beam generated by the sub-array is different from 90° so that Doppler frequency signals would be enhanced.

The backscattered ultrasound waves can be received by means of a sub-array, which can be a different sub-array than the one for transmitting the ultrasound beam or by the entire array, in order to have as much signal intensity as possible for the received signals.

The above mentioned general principle is explained using a simplified special example of a linear array illustrated in FIGS. 2 and 3. The skilled person will be able to extend the teaching of said example to the general case that was discussed above.

FIG. 2 shows an array 1 of electro-acoustic transducer elements, which is composed of individual electro-acoustic transducer elements 101. In the illustrated embodiment, 64 transducer elements are provided, the first of which is designated by numeral 101(1) and the last by numeral 101(64).

The probe is preferably of the phased array type, such as probe PA240 manufactured by Esaote S.p.A. Each transmitting transducer element has an independent line for feeding electric excitation pulses, which are supplied thereto from an excitation section as described below.

Considering the line of view LV, which coincides, in this example, with the center axis of the array 1 of the transducer elements 101(1) to 101(64) and divides said array 1 into two halves, each with 36 transducer elements, from 101(1) to 101(36) and from 101(37) to 101(64) respectively, this line of view LV is orthogonal to the direction of the flows F1 and F2 in the two vessels V1 and V2 intersected by said line of view. Therefore, by successively focusing the beam of transmit ultrasonic pulses generated by the entire array 1 of transducer elements to said line of view LV at the depths defined by the focusing points 2 arranged along said line of view LV, no flow direction information can be retrieved from Doppler frequency shift data. As shown in FIG. 1, the line of view LV forms angles θLV of 90° with the flows F1 and F2 in the vessels V1 and V2.

A schematic and simplified representation of beam focusing would be similar to the one shown in FIG. 2, which is a simplified and schematic example of focusing during reception.

In order to introduce an angle of incidence of the transmit ultrasonic pulse beam that is other than 90°, according to the present invention, only some of the 64 electro-acoustic transducer elements 101 are used, which form a sub-array of transmitting electro-acoustic elements in direct side-by-side relation, and whose transmitting surface is eccentric in relation to the center axis of the overall array 1 of electro-acoustic transducers, i.e. the overall transmitting surface. In the illustrated embodiment, said sub-array of electro-acoustic transducer elements comprises the electro-acoustic transducer elements of one of the two halves of the array 1 on one of the two sides of the center axis LV. Particularly referring to FIG. 1, said sub-array comprises the electro-acoustic transducer elements 37 to 63, designated by numerals 101(37) to 101(64).

In this case, the axis of the transmit pulse beam is defined as the axis that starts from the center point of the transmitting surface of the electro-acoustic transducer elements of said sub-array, with the center axis AC (shown as a broken line) of said sub-array, designated as 1' in FIG. 1, passing through said point.

It will be appreciated that, assuming a line of view LV and the foci 2 thereon, focusing the beams of transmit ultrasonic pulses, transmitted by the electro-acoustic transducer elements of the sub-array 1' only, causes the direction of propagation of the acoustic front, i.e. the axis AF of each of the beams of transmit ultrasonic pulses successively focused to said foci 2 on the line of view LV, to form an angle OAF with the directions of blood flows F1 and F2, which is other than 90°, and in this case smaller than 90° when the line of view LV is perpendicular to the directions of the blood flows F1 and F2.

During reception, as shown in FIG. 3, the entire array 1 is used and the receiving electro-acoustic transducer elements are actuated to focus the receive ultrasonic pulse beams to the axis that coincides with the line of view LV, here coinciding with the center axis perpendicular to the transmitting surface of the entire array 1. Alternatively, a sub-array having a different aperture then the sub-array used during transmission or the aperture of the entire array cam be used also for receiving the back-scattered ultrasound beams.

By this arrangement, slight steering of transmit pulse beams is introduced, and causes a further polarization of Doppler information as a function of the direction of the blood flow under examination.

Steering angles are relatively small, of the order of 83 to 87°, or (180-83)° to (180-87)°. A slight Doppler frequency shift occurs whereby, using prior art technologies such as Color Flow Mapping or spectral Doppler technologies such asmultigate, flow direction information will be difficult to be extracted.

In the case of Color Flow Mapping technologies, which determine the average frequency value at one point, in order to reach sufficient signal sensitivity, the pulse repetition frequency (PRF) shall be maintained at a low value, whereas retrieval and display of flow direction information introduced by the above described steering would require a high pulse repetition frequency (PRF), which would cause an excessive sensitivity reduction and hence signal losses.

In the case of spectral Doppler imaging technologies, such as the technology known asmultigate, the above described steering is of no use in making spectral profiles asymmetric with respect to the zero axis, i.e. to a zero shift or a zero flow velocity.

On the contrary, using said steering method of the transmit and/or backscattered beam in combination with the method according to the present invention, consisting in extracting the mean Doppler frequency from the Doppler frequency signals and representing said mean Doppler frequency as a function of the corresponding sample volume along the penetration depths of the transmit beam by enhancing the appearance of said image, provides improved and clear indication of the direction of motion when the angle of incidence of the transmit beam is very close to 90° relative to said direction of motion.

FIG. 3 schematically shows an ultrasound imaging system adapted for implementing the method of the present invention.

Also in this case, the functional sections provide features and constructions known per se and widely used.

An ultrasonic probe comprises an array 1 of electro-acoustic transducer elements. The probe is preferably of the phased array type and the transducers are each connected, separately from the other ones and via a switch 12, alternately to a transmit beamformer 16 and a receive beamformer 13. The transmit beamformer 16 receives electric excitation pulses for the electro-acoustic transducer elements of the array 1 from a pulse generator 17. The pulses are fed to the individual transducers according to a particular mode, i.e. with excitation delays set for each electro-acoustic transducer element, so that the pulse beam is focused along a predetermined line of view or successively along a plurality of adjacent lines of view to cover a two-dimensional area. Selection is dependent upon the desired imaging mode.

Excitation pulses are also repeated with a predetermined frequency, also in this case according to known methods, widely used in current ultrasound imaging apparatus. In FIG. 3, two sections 18 and 19 are indicated in differentiated manners to show that forming and excitation of electro-acoustic transducer elements for Doppler imaging are different from those traditionally used and particularly from those used for generation of anatomic or B-mode images. Particularly, such excitation methods are those previously described with reference to FIG. 1. The one or more lines of view and the foci of the transmit ultrasonic pulse beams on said line/s of view may be manually selected in a user-customized manner. Otherwise, the user may select among different combinations of fixed settings, which are stored for selection, or the apparatus automatically sets said parameters when the Doppler imaging feature is set. The above is embodied by section 20, which may be a data input interface for a user or a memory that automatically provides the parameters for setting the line of view and the foci.

During reception, the beamformer 13 is also controlled by a section that supplies the focusing data as described above. Particularly, as shown by the two sections 14 and 15, the methods for focusing the receive pulse beam may be different for Doppler imaging according to the method of the present invention and for parallel B-mode imaging.

The receive signals that come out of the receive beamformer are processed in a known manner to obtain the desired image. Processing for retrieving image data and converting it into images to be displayed on the screen 27 is known per se and will not be described in further detail, because the knowledge of such processing is part of the know-how of a person of ordinary skill in the art.

The receive signals are processed by a multigate Doppler processor designated by numeral 21, which retrieves spectral profile information from Doppler shifts at various penetration depths. As shown by the functional unit 24, image data is generated for display of said spectral profiles, as shown in FIG. 3 and FIG. 4, whereas numeral 25 designates a section for determining the average frequency from the spectral Doppler shift profiles for at least some penetration depth ranges and particularly for those that coincide with the flows detected from spectral profiles. An image processing section 26 converts said spectral profile data and spectral average data for said profiles into images to be displayed.

The sections 24 and 25 and, concerning the image, the section 26 also carry out one or more processing steps among those provided and listed above, and particularly perform the steps of:

attenuating the display of the spectral profile, as compared with standard display, to enhance the overlapped average;

strongly filtering out the low frequency components of the spectrum to extract a more significant average;

enhancing the average components in terms of range to give clear direction information;

introducing an asymmetric persistence, that enhances flow arrival (typically during forced inspiration) and "maintains" it as it decreases.

A B-mode image processor 23 may be provided and may allow the B-mode image to be displayed adjacent to multigate Doppler images, through the image processing section 26.

Possibly, as shown by a box outlined by broken lines 22, an image processing unit may be provided for generating Color Flow Mapping (CFM) images, which may be displayed over the B-mode image.

The means 20 for the input of line of view of focus parameters may be equipped with a graphical user interface, which allows plotting both the line of view and the individual foci therealong on the B-mode image. The graphical input data are both displayed and converted into parameters to be fed to the transmit beamformer 16 through the focusing control sections 19.

In another improvement, the system of FIG. 3 is further provided with a graphic user interface and means such as a mouse or similar for drawing a line of view LV on a B-mode image. Furthermore, the system can be provided with means for graphically drawing on the line LV several depth increments such as the ones indicated with numeral 2 on FIG. 1. The image processor 26 determines the geometric parameters such as orientation and position relative to the B-mode image of the drawn lines and depth increments. These data may be converted by the scanline and range gate input data unit 20 in corresponding settings of the ultrasound systems relative to the transmit beamformer 16 and to the multigate processor 21.

Furthermore, depending on the orientation of the line of view LV and the position of the chosen depth increments on said line, the system can determine automatically which of the single transducers of the array of transducers 1 has to be activated as an element for a sub-array of transmit and or receipt transducers to enhance polarization of the flow direction information in the Doppler signal samples.

The above determined settings and the selected transducers for forming transmit and/or receipt sub-arrays having different apertures can be changed automatically during scanning operations if a reduction in the polarization of the direction information is determined. This could be evaluated by monitoring the maximum mean frequency across the lumen of a vessel or an average value of the mean frequency profile across the lumen of a vessel.

An additional improvement the system according to FIG. 3 could be provided with means for tracking the position and orientation of the probe carrying the array of transducers. This means that the position and orientation of the array of transducers and of the beam generated by said array can be tracked. Thus, the system allows tracing of an optimal desired line of view by the graphic user interface and also tracking if the probe is held by the user in a correct way, so that the transmitted beam is oriented along the chosen line of view. The line of view generated by the probe can be displayed on the B-mode image helping the user in displacing the probe and thus the array of transducers, in such a way that the generated ultrasound beam is oriented along the chosen line of view. When the two lines come to coincide, the image processor can be designed to generate a trigger output signal, which starts the imaging process for transmitting and receiving the ultrasound signals and displaying the Doppler velocity information.

The invention claimed is:

1. A method of acquiring and displaying Doppler data from a subject under study through an ultrasound system, the method comprising the following steps:
    a) transmitting ultrasound waves into the subject under study;
    b) generating back-scattered signals in response to a back-scattering of the ultrasound waves from the subject under study;
    c) generating a plurality of Doppler signal samples representing a predetermined range of depth increments within said subject in response to said back-scattered signals;
    d) generating a plurality of first Doppler frequency signals representing said predetermined range of depth increments in response to said Doppler signal samples;
    e) displaying a first Doppler graph representing said first Doppler frequency along a first axis and said range of depth increments along a second axis in response to said first Doppler frequency signals;
    f) generating Doppler mean frequency signals at each of the range depth increments from the first Doppler frequency signals;
    g) displaying a second Doppler graph representing said Doppler mean frequency along the first axis and said range depth increments along the second axis by setting parameters defining a status of appearance of pixels forming a displayed image of the second Doppler graph that visually differentiates the pixels from pixels of an image of the first Doppler graph;
    h) displaying and maintaining appearance of the pixels forming the image of said second Doppler graph such that the pixels maintain their status of appearance regardless of any attenuation or termination of said first Doppler frequency signals for a predetermined period of time, or until second Doppler frequency signals with greater absolute mean frequency values than said first Doppler frequency signals are generated from Doppler signal samples acquired during a repetition of steps a) to q),
    wherein said Doppler mean frequency signals are used to upgrade the displayed image of said second Doppler graph by setting the status of the appearance of the pixels forming said displayed image of said second Doppler graph.

2. The method according to claim 1, further comprising the step of filtering out a predetermined frequency component of the first Doppler frequency signals before generating the Doppler mean frequency signals.

3. The method according to claim 1, wherein the step g) comprises enhancing brightness of the pixels forming the image of the second Doppler graph.

4. The method according to claim 3, further comprising the step of reducing brightness of the pixels forming the image of the first Doppler graph.

5. The method according to claim 1, further comprising the step of changing representation of frequency along the first axis representing the values of the Doppler mean frequency of the Doppler mean frequency signals.

6. The method according to claim 5, wherein the scale is enlarged in order to enlarge dimensions of the image of the second graph in relation to the dimensions of the first graph along the first axis.

7. The method according to claim 1, wherein the subject under study comprises at least a blood vessel and blood flux in the blood vessel having a flux velocity varying in time between a maximum velocity and a velocity which is approximately zero or in an opposed direction,
wherein the predetermined range of depth increments is set to cover an entire cross section of the at least one vessel;
wherein the first Doppler frequency signals and the Doppler mean frequency signals are representative of the velocity of the blood flux in the vessel at the depth increments; and
wherein the step of maintaining appearance of the pixels forming the image of the second Doppler graph comprises maintaining appearance until second Doppler frequency signals with greater absolute mean frequency values than said first Doppler frequency signals are generated from Doppler signal samples acquired during at least one of the repetitions in step h) coinciding with a blood flux velocity that is larger, in absolute value, than the blood flux velocity during the step of generating said first Doppler frequency signals.

8. The method according to claim 1, wherein said back-scattered signals are received from a first region of interest within said subject resulting in said Doppler signal samples and from at least second or more further regions of interest within said subject.

9. The method according to claim 8, wherein said transmitted ultrasound waves comprise an ultrasound beam optimized for Doppler data acquisition which is directed along a direction crossing at least two or more of the regions of interest.

10. The method according to claim 8, wherein the regions of interests are different blood vessels, a plurality of Doppler signal samples being generated in response to said back-scattered signals representing a predetermined range of depth increments each one of which crosses at least partially one of the blood vessels.

11. The method according to claim 1, further comprising the steps of:
generating B-mode data for a region of interest containing the subject under study;
acquiring and displaying the B-mode data from the subject under study; and
displaying a B-mode image and further displaying, in a superimposed way on the B-mode image, a scan line along which a Doppler beam is focused and the range of depth increments on corresponding regions of interest.

12. The method according to claim 1, further comprising the step of providing a transmit and a receive array of ultrasound transducers, the array having a predetermined aperture, the ultrasound waves being transmitted using a first sub-array of the array of ultrasound transducers, the first sub-array being formed by only a part of the ultrasound transducers of the array and having a first aperture different from the aperture of the array of ultrasound transducers and generating an ultrasound beam having a direction of propagation which is different from a direction of propagation of an ultrasound beam generated by the complete array of transducers, the direction of propagation of the ultrasound beam emitted by the first sub-array being set to at least partially cross one or more regions of interest within the subject under study,
wherein back-scattered ultrasound beams are received by a second sub-array of the receive array of transducers or by the complete receive array.

13. The method according to claim 12, wherein the second sub-array is different from the first sub-array.

14. The method according to claim 13, wherein the transmit and receive array of transducers comprises a same array of ultrasound transducers in combination with a switch connecting alternatively the ultrasound transducers of the array to a generator of excitation signals of the ultrasound transducers and to a processing device of receipt signals generated by back-scattered ultrasound waves impinging on the ultrasound transducers.

15. An apparatus for carrying out the method for ultrasonic detection and imaging of hemodynamic information, particularly venous blood flow information, as claimed in claim 1, the apparatus comprising:
an ultrasonic probe comprising an array of transmitting and receiving electro-acoustic transducers, the transducers being arranged according to a predetermined order and design, each transmitting electro-acoustic transducer having its own independent line for connection to a unit that generates and transmits electric excitation signals, each receiving electro-acoustic transducer having its own independent line for connection to at least one processing unit;
at least one unit configured to provide multigate processing of image data and to generate Doppler frequency signals from the Doppler signal sample received from sample volumes at different depths increments;
said at least one processing unit being configured to calculate an average frequency of signals of the Doppler frequency signals relating to at least some of the sample volumes; and
a unit configured to display a first Doppler graph representing said Doppler frequency along a first axis and said range of depth increments along a second axis in response to said Doppler frequency signals, and to display a second Doppler graph representing said Doppler mean frequency along said first axis and said range depth increments along said second axis by setting the parameters defining a status of appearance of the pixels forming the displayed image of said second Doppler graph differently from the parameters defining the status of appearance of the pixels forming the displayed image of said first Doppler graph.

16. The apparatus according to claim 15, further comprising:
a unit configured to transmit and receive electro-acoustic pulse beams for anatomic B-mode imaging;
a unit configured to process received signals and generate B-mode image data; and
a device configured to display the B-mode image in side-by-side relation with the image that displays average frequencies of spectral profiles of Doppler shift frequencies and the spectral profiles of Doppler shift frequencies as a function of the penetration depth of the transmit ultrasonic pulse beam.

17. The apparatus according to claim 15, further comprising:
a unit configured to graphically draw a line on the B-mode image and to select said line as the line along which a beam for Doppler data acquisition has to be focused;
a unit configured to select a predetermined range of depths increments along said line at one or more regions of said line;
a unit configured to calculate the beam focusing parameters for driving the transducers of the array of the probe to focus the beam at said line and for setting a receive signal processing unit of an ultrasound apparatus to extract and process a receipt signal contribution relating to ultrasound beams back-scattered from each of the sample volumes corresponding to the depths increments;
a unit configured to track a position and an orientation of the probe and to determine the orientation of the line along which an ultrasound transmit beam will be focused and for displaying the line on the be mode image; and a unit configured to trigger the transmission of the ultrasound transmit beam when the line on which the beam is focused coincides with the line drawn on the B-mode image.

18. The apparatus according to claim 17, further comprising:

a first switching unit connecting to the unit that generates and transmits electric excitation signals a number of selected transducers less than a total numbers of transducers of the array, the number of transducers being selected to form a sub-array of transducers having an aperture which is different from the aperture of the complete array of transducers and eccentric relatively to a center of the array of transducers; and a second switching unit connecting to the unit for processing receipt signals to a number of selected transducers of the array of receipt transducers, the number of transducers being selected to vary the number of transducers from the total number of transducers to a number less than the total number of the transducers in order to form a sub-array of transducers having an aperture which is different from the aperture of the complete array of transducers and eccentric relatively to the center of the array of transducers.

19. The apparatus according to claim 18, wherein the switching means are automatically driven by control means which vary the number of selected transducers of one or more of the array of transmit transducers or the array of receipt transducers by computing corresponding aperture from data determined by a physical law of propagation of acoustic waves and orientation of a line drawn on the B-mode image along which the transmit beam has to be focused and a position on that line of sample volumes defined by the range of depth increments.

20. The apparatus according to claim 15, further comprising a device that varies a number and a position on the array of the transmit and or receipt transducers to be selected for maximizing the value of a maximum detected mean Doppler frequency.

* * * * *